(12) United States Patent
Rapp

(10) Patent No.: US 10,201,626 B1
(45) Date of Patent: Feb. 12, 2019

(54) PORTABLE ULTRA VIOLET C SANITIZER

(71) Applicant: Luke Edward Rapp, Bethlehem, WV (US)

(72) Inventor: Luke Edward Rapp, Bethlehem, WV (US)

(*) Notice: Subject to any disclaimer, the term of this patent is extended or adjusted under 35 U.S.C. 154(b) by 185 days.

(21) Appl. No.: 15/436,848

(22) Filed: Feb. 19, 2017

(51) Int. Cl.
- *A61L 2/10* (2006.01)
- *A61L 2/00* (2006.01)
- *A61L 2/24* (2006.01)
- *G01J 1/42* (2006.01)

(52) U.S. Cl.
CPC .......... *A61L 2/10* (2013.01); *A61L 2/24* (2013.01); *G01J 1/429* (2013.01); *A61L 2202/11* (2013.01); *A61L 2202/122* (2013.01); *A61L 2202/14* (2013.01); *A61L 2202/16* (2013.01)

(58) Field of Classification Search
USPC .... 250/453.11, 455.11, 461.1, 492.1, 504 R, 250/504 H; 607/93, 94, 98–100; 422/1, 422/24, 105, 109, 120
See application file for complete search history.

(56) References Cited

U.S. PATENT DOCUMENTS

| | | | | |
|---|---|---|---|---|
| 4,033,719 A * | 7/1977 | Conn | ...................... | A01K 63/04 210/167.26 |
| 7,622,892 B2 * | 11/2009 | Kim | ...................... | H02J 5/005 320/108 |
| 9,265,850 B2 * | 2/2016 | Davis | ...................... | A61L 2/10 |
| 2010/0061887 A1 * | 3/2010 | Harper | ...................... | A61L 2/10 422/24 |
| 2014/0264084 A1 * | 9/2014 | Davis | ...................... | A61L 2/10 250/492.1 |

* cited by examiner

*Primary Examiner* — Bernard Souw

(57) ABSTRACT

The Portable Ultra Violet C Sanitizer is a self-contained, portable, self-shut-off, preprogrammed/programmable UVC light irradiation microorganism inactivation device that more effectively, efficiently and safely sanitizes surfaces than comparable products presently on the market. Advantageously, the device provides a faster alternative for UVC sterilization of a surface, while protecting the operator from potentially dangerous exposure to the UVC radiation.

1 Claim, 5 Drawing Sheets is a schematic view, showing how the device functions

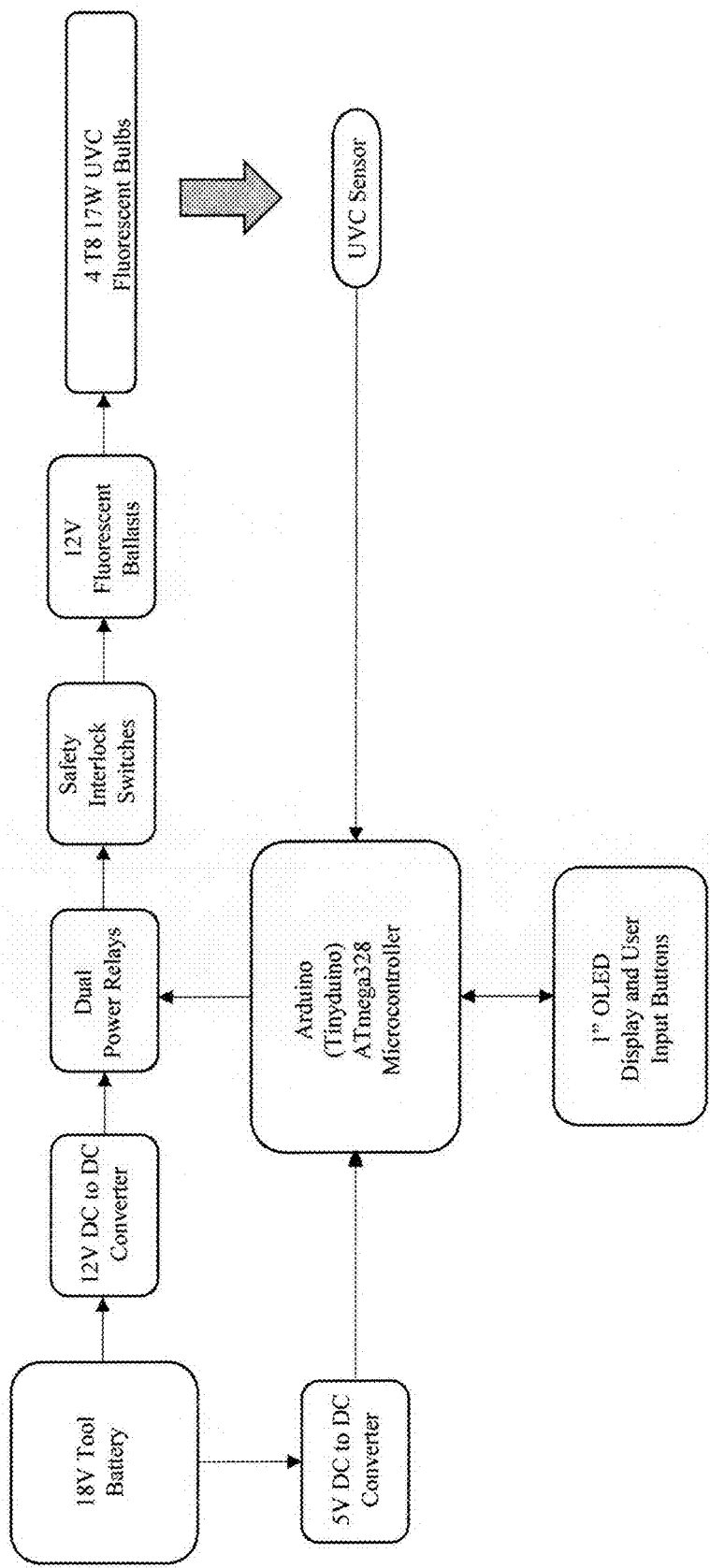
FIG. 1 block diagram of the present invention

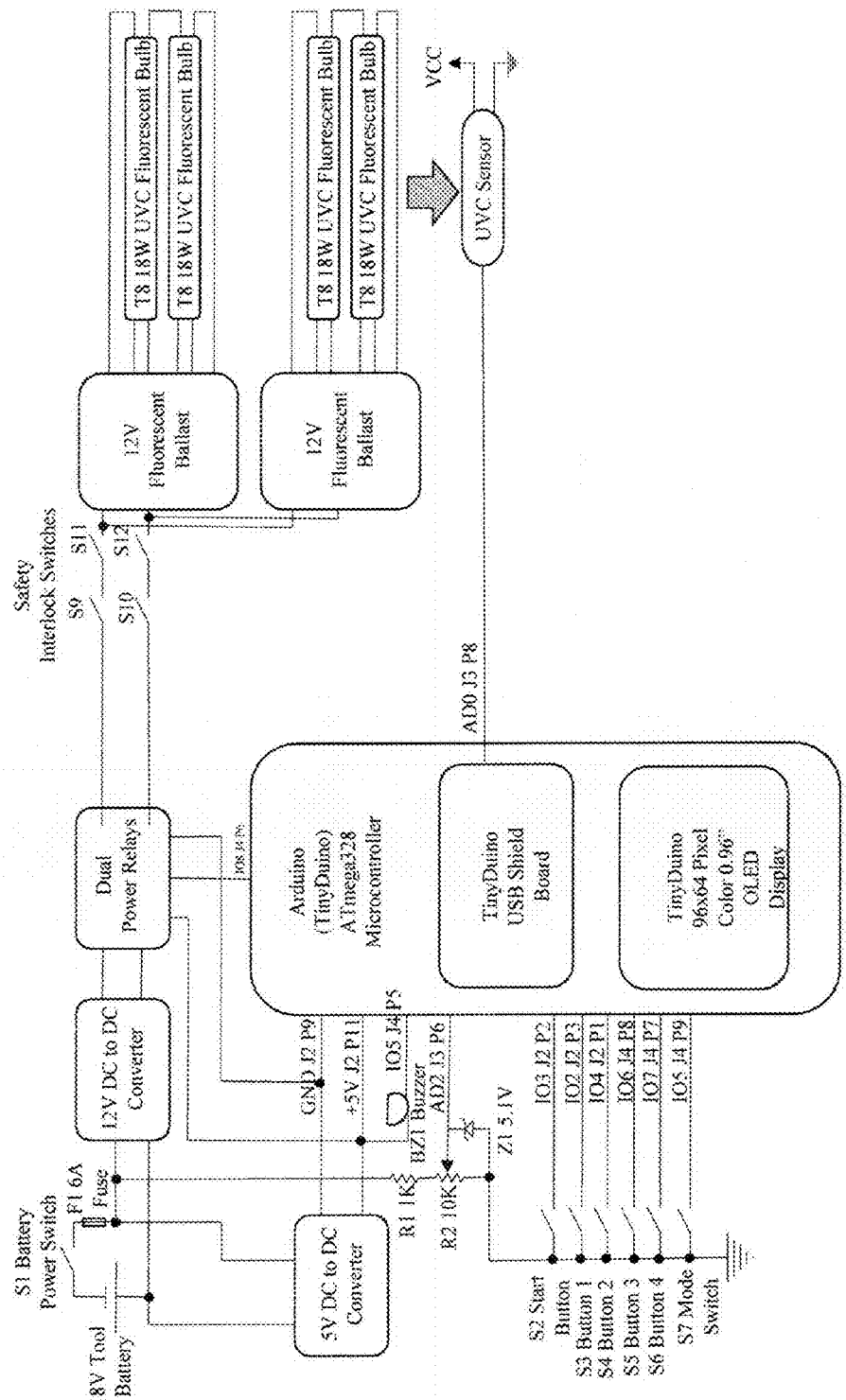
FIG. 2 is a schematic view, showing how the device functions

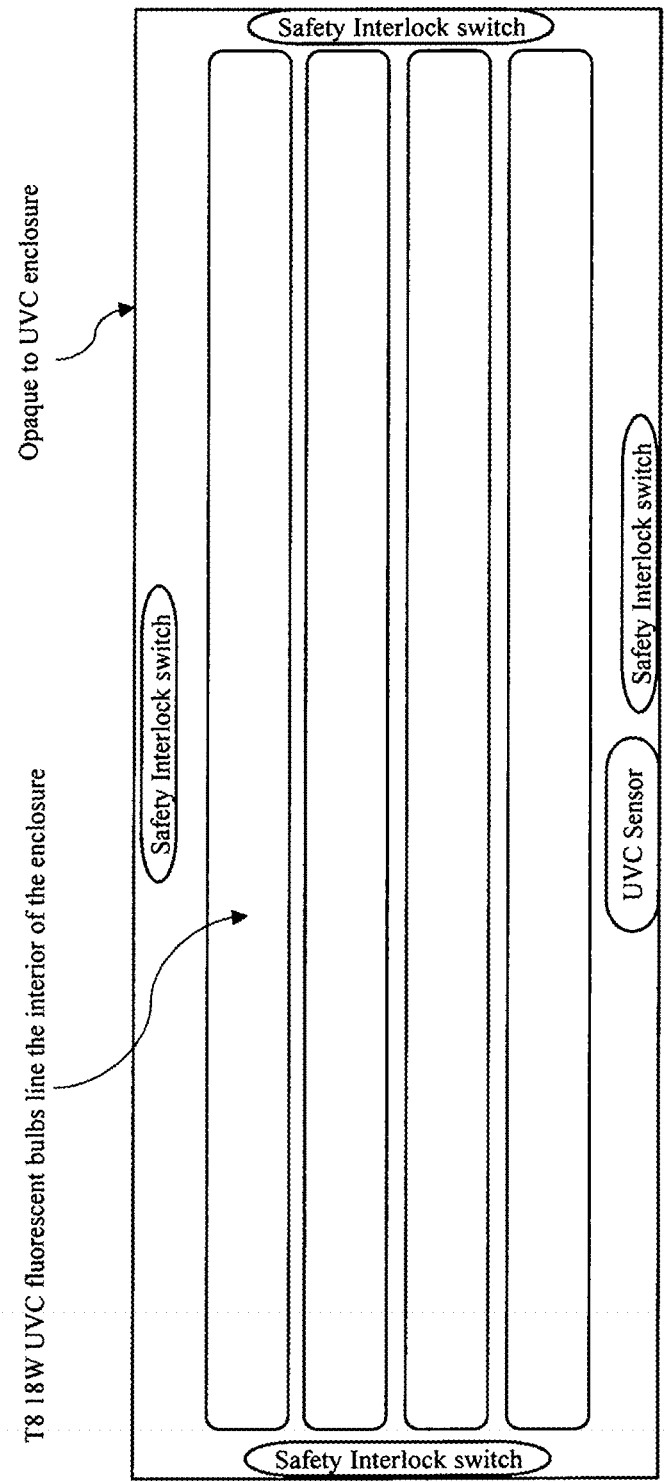
FIG. 3 is an isometric view from underneath, showing the UVC light source

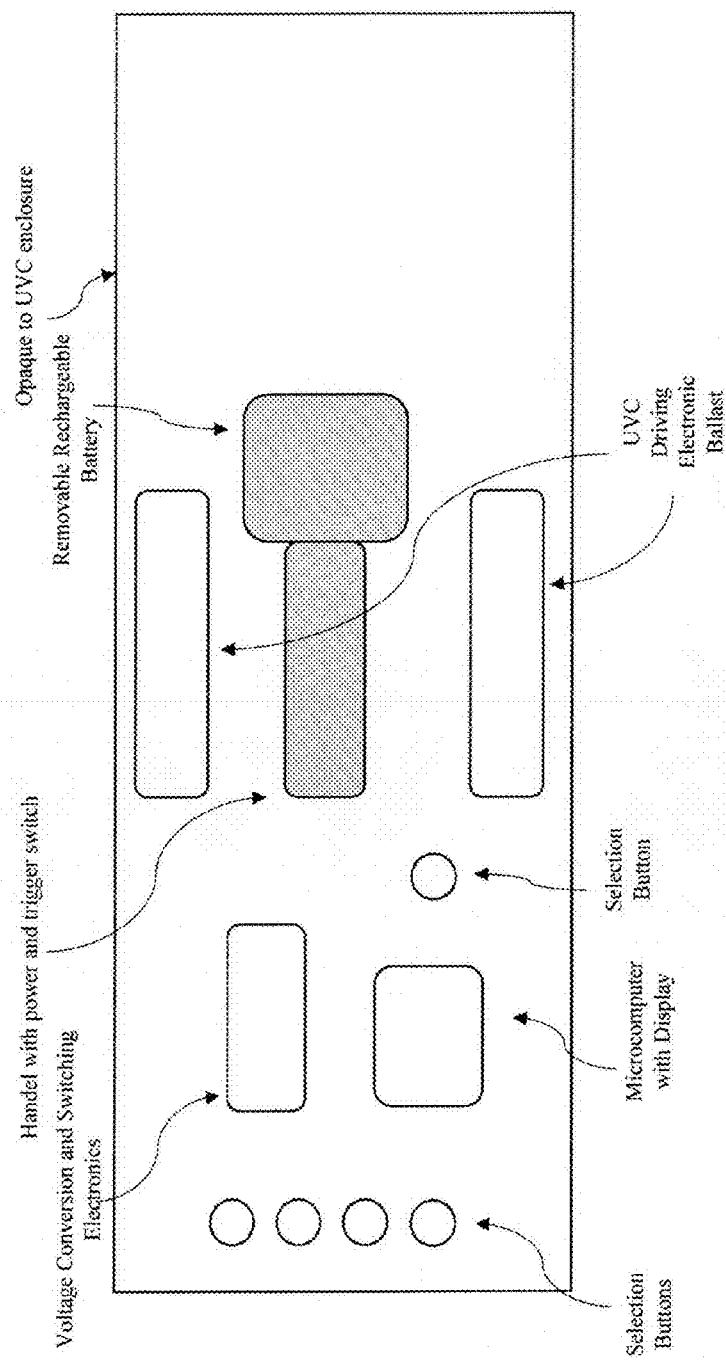
FIG. 4 is an isometric view, showing the top of the present invention

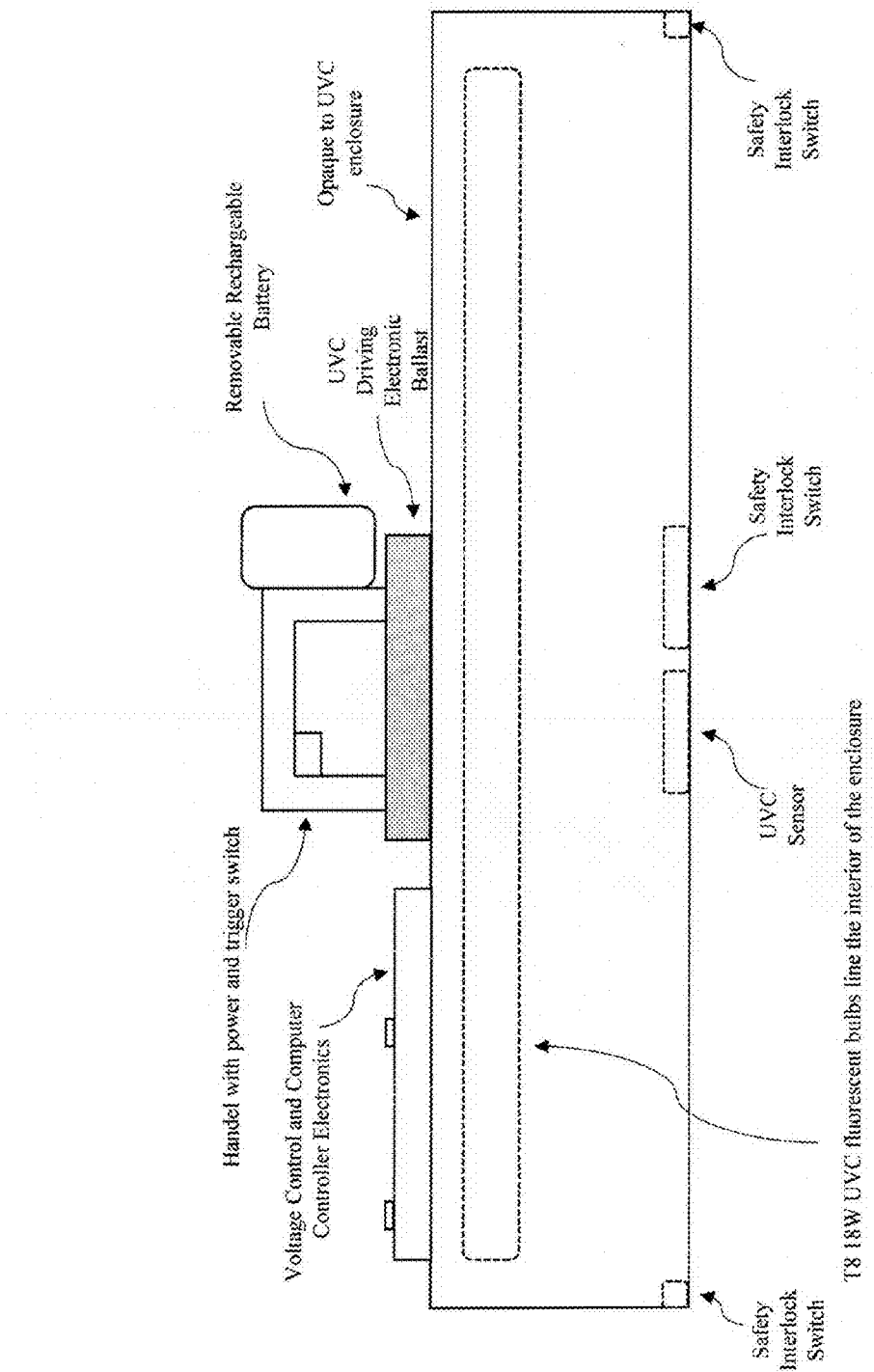

PORTABLE ULTRA VIOLET C SANITIZER

BACKGROUND OF THE INVENTION

1. Field of the Invention

This invention relates to the field of ultra violet sanitation devices. More specifically, the invention comprises a self-contained, portable, preprogrammed, Ultra Violet C (UVC), sterilization chamber which conveniently and safely sanitizes the surface of contents placed within the device.

2. Description of the Related Art

There are portable ultra violet light wands on the market for sanitizing surfaces. However, the portable wands claim they take a few seconds to sanitize surfaces, when in actuality, they need to remain positioned over a surface for more approximately 20 seconds at a distance of no more than approximately one inch (depending upon the intensity of the bulb) to effectively inactivate microorganisms, and this only happens directly at the space under the wand, where the wand beam is positioned. Wands do not protect users from attenuation and the dangers of UVC rays, as the light is not contained, but spills out from the sides of the wand. Additionally, wands may be dangerously aimed at people. Permanently mounted keyboard UVC sanitation devices exist on the market; however, they are not portable, preprogrammed, and they don't offer safety protection for the user.

The portable UVC sanitizer seeks to provide a user-safe, more efficient and effective UVC sanitation alternative device, with unique preprogramed/programmable disinfection functions—offering a remedy to the shortcomings in existing UVC portable and stationary sanitation devices.

BRIEF SUMMARY OF THE PRESENT INVENTION

The portable UVC sanitizer is a self-contained, portable, self-shut-off, preprogramed/programmable UVC light irradiation microorganism deactivation device that more effectively, efficiently and safely sanitizes surfaces than comparable products on the market.

It is more effective and efficient because of its design. The light source, encased in a protective housing, is monitored by a UVC sensor when the lights are activated. This allows for the lights to be shut off once the desired amount of UVC exposure for sterilization of a surface has been reached—providing the optimal amount of sterilizing rays to achieve microorganism deactivation, while minimizing materials' exposure and photochemical degradation of items within its sanitizing chamber. This efficient way of sterilization is made possible by preprogramed doses of UVC. The device can be programmed to deactivate a certain contaminant or range of contaminants on the surface. This means that the device will turn the lights on and they will remain on until the dose of UVC light required to deactivate that containment has been reached.

Enhanced user safety is factored into the design. The device's encasing allots space for multiple UVC light sources, from which the user is completely protected by the unit's housing, preventing any exposure to the UVC light. Power for the light sources is derived from a removable and rechargeable battery.

BRIEF DESCRIPTION OF THE SEVERAL VIEWS OF THE DRAWINGS

FIG. 1 is a block diagram of the present invention
FIG. 2 is a schematic view, showing how the device functions
FIG. 3 is an isometric view from underneath, showing the UVC light source
FIG. 4 is an isometric view, showing the top of the present invention
FIG. 5 is an isometric view, showing the side of the present invention

DETAILED DESCRIPTION OF THE INVENTION

The terminology used herein is for the purpose of describing particular embodiments only and is not intended to be limiting of the invention. The present disclosure is to be considered as an exemplification of the invention, and is not intended to limit the invention to the specific embodiments illustrated by the figures or descriptions below. The present invention will now be described by referencing the appended figures representing preferred embodiments.

FIG. 1 is a block diagram of the present invention. Power flows from the battery to the DC to DC converters which then goes to the microcontroller and dual power relays. Once the relays are energized, the power then flows through the safety switches. If the safety switches are depressed, the light bulbs will then be energized and the deactivation process will begin. Once the process initiates, the UVC sensor will begin to measure the amount of UVC light administered and automatically disengage the lights when the predetermined dose has been reached.

FIG. 2 shows a schematic view of the instrumentation and how each component works with the others to perform the end function. The process begins with energy flowing from the battery into the DC to DC converters. One DC to DC converter supplies power to the microcontroller, the other supplies power to the relays. Once the dose of UVC has been selected, via the selection buttons mounted on the device, and the sterilization procedure is initiated, the UVC sensor begins to monitor the UVC light, the relays are tripped, sending power to the ballasts, causing the UVC lights come on. The microcontroller will disengage the relays once the predetermined dose of UVC has been reached, ending the process.

FIG. 3 is an isometric view from underneath, showing the UVC light source. This embodiment protects the user from the potentially harmful UVC rays and, also, houses safety sensors located around the edges and the UVC sensor mounted along one side.

FIG. 4 shows a close-up view of the instrumentation that manages the sanitation process, including the microcontroller, selection buttons, relays, DC to DC converters and other various electronic equipment, such as resistors, capacitors, wiring, etc.

FIG. 5 is an isometric view showing an image representing the elongated sides of the device. This view highlights features such as the integrated handle for ease of use, the removable battery for convenience, the opaque protective enclosure, and the relative location of instruments when viewed from the side.

Having described my invention, I claim:
1. A self-contained, portable, Ultra Violet C light sterilization chamber, which uniquely actively measures and monitors administration of the UVC dose to ensure it only administers the minimally effective UVC dose required to biologically deactivate the surface of the article placed within the chamber; comprising:

a. An integrated UVC sensor, coupled with a microcontroller, to ensure the minimal UVC dose required to deactivate the target organism has been successfully administered, while preventing unnecessary damage to the article be decontaminated
b. A housing designed to completely cover the item to be sanitized, so as to protect the user from UVC exposure of any kind
c. A series of safety switches/interlocks designed to turn off the lights to protect the user and others from accidental harm due to UVC exposure, if the device's full sealing contact with a table or underneath surface becomes compromised
d. A pre-programmed system designed to disengage the lights after the set dose of UVC exposure required to deactivate the selected contaminant has been reached
e. An easily removable and rechargeable battery power source
f. An adequate amount of UVC light providing high intensity to be discharged from the source to enable a minimal time required for sterilization.

\* \* \* \* \*